United States Patent [19]
Bailey et al.

[11] Patent Number: 5,982,843
[45] Date of Patent: Nov. 9, 1999

[54] CLOSED LOOP AIR CONDITIONING SYSTEM FOR A COMPUTED TOMOGRAPHY SCANNER

[75] Inventors: Eric M. Bailey, Hampstead, N.H.; Andrew P. Tybinkowski, Boxford, Mass.

[73] Assignee: Analogic Corporation, Peabody, Mass.

[21] Appl. No.: 08/948,692

[22] Filed: Oct. 10, 1997

[51] Int. Cl.⁶ .................................................. G01N 23/00
[52] U.S. Cl. .............................................. 378/4; 378/210
[58] Field of Search ........................................... 378/4–20

[56] References Cited

U.S. PATENT DOCUMENTS 4,969,167  11/1990  Zupancic ................................... 378/10
5,577,026  11/1996  Gordon et al. ............................. 370/24

Primary Examiner—Craig E. Church
Attorney, Agent, or Firm—Lappin & Kusmer LLP

[57] ABSTRACT

A computed tomography (CT) scanner includes an enclosure which forms a substantially sealed chamber around the rotatable disk carrying the radiation source and the radiation detectors. The CT scanner further includes an air conditioning system for controlling the temperature and humidity of the air inside the chamber. The air conditioning system can be a closed loop system whereby only air from inside the chamber is processed through the air conditioning system and no outside air is introduced to the chamber. Thus, the CT scanner can be operated in a wider range of environmental conditions. In an alternate embodiment, the air conditioning system can produce a positive pressure inside the chamber to prevent outside air from entering through openings in the enclosure. In this embodiment, the air conditioning system can include an input port in order to draw sufficient outside air to produce a positive pressure inside the chamber. The input port can include a filter to prevent dust from entering the chamber, thus, enabling the CT scanner to have a longer useful life between preventative maintenance and service events.

10 Claims, 5 Drawing Sheets

CLOSED LOOP AIR CONDITIONING SYSTEM FOR A COMPUTED TOMOGRAPHY SCANNER

CROSS-REFERENCE TO RELATED APPLICATIONS

This application is related to U.S. Pat. No. 5,432,339; copending U.S. application Ser. No. 08/671,716, filed on Jun. 27, 1996; copending U.S. patent application Ser. No. 08/831,558, filed on Apr. 9, 1997; and the following U.S. applications filed on even date herewith, of common assignee, the contents of which are incorporated herein in their entirety:

This application is related to the following U.S. applications filed on even date herewith, of common assignee, the contents of which are incorporated herein in their entirety by reference:

"Computed Tomography Scanner Drive System and Bearing," invented by Andrew P. Tybinkowski, et al., (Attorney Docket No. ANA-128);

"Air Calibration Scan for Computed Tomography Scanner with Obstructing Objects," invented by David A. Schafer, et al., (Attorney Docket No. ANA-129);

"Computed Tomography Scanning Apparatus and Method With Temperature Compensation for Dark Current Offsets," invented by Christopher C. Ruth, et al., (Attorney Docket No. ANA-131);

"Computed Tomography Scanning Target Detection Using Non-Parallel Slices," invented by Christopher C. Ruth, et al., (Attorney Docket No. ANA-132);

"Computed Tomography Scanning Target Detection Using Target Surface Normals," invented by Christopher C. Ruth, et al., (Attorney Docket No. ANA-133);

"Parallel Processing Architecture for Computed Tomography Scanning System Using Non-Parallel Slices," invented by Christopher C. Ruth, et al., (Attorney Docket No. ANA-134);

"Computed Tomography Scanning Apparatus and Method Using Parallel Projections from Non-Parallel Slices," invented by Christopher C. Ruth, et al., (Attorney Docket No. ANA-135);

"Computed Tomography Scanning Apparatus and Method Using Adaptive Reconstruction Window," invented by Bernard M. Gordon, et al., (Attorney Docket No. ANA-136);

"Area Detector Array for Computed Tomography Scanning System," invented by David A Schafer, et al., (Attorney Docket No. ANA-137);

"Measurement and Control System for Controlling System Functions as a Function of Rotational Parameters of a Rotating Device," invented by Geoffrey A. Legg et al., (Attorney Docket No. ANA-139);

"Rotary Energy Shield for Computed Tomography Scanner," invented by Andrew P. Tybinkowski, et al., (Attorney Docket No. ANA-144).

STATEMENT REGARDING FEDERALLY SPONSORED RESEARCH

Not Applicable

REFERENCE TO MICROFICHE APPENDIX

Not Applicable

BACKGROUND OF THE INVENTION

This invention relates to Computed Tomography (CT) Scanners and, more particularly, to a tomography system which can be used in a wide range of environmental conditions.

A CT scanner is a device used to generate an image of a cross-section of an object. Such devices are well known for use in the field of medicine for non-invasive diagnosis of patients. The typical CT scanner includes a rotatable disk mounted for rotation on a support frame. The disk includes a central aperture in which an object to be scanned, typically a human patient is positioned. An X-ray source is mounted to the rotatable disk and projects a beam of X-ray radiation into the object from a plurality of positions around the object. A plurality of X-ray detectors, either positioned on the rotatable disk diametrically opposite to the position of the X-ray source or positioned on the support frame at locations around the rotatable disk, produce data signals representative of the X-ray radiation that passes through the object. Using well known techniques, these data signals can be used to produce an image of a cross-section of the object which has been scanned by the system.

In at least one commercial system, the rotatable disk carries the X-ray source, typically an X-ray tube, a power supply for the X-ray tube, an array of X-ray radiation detectors, a data acquisition system (DAS), a power supply for the radiation detectors and the DAS and may carry other support systems as well. The power supplies of the commercially available scanner are electrically coupled via a power bus to a source of power provided at the support frame such as a conventional 120 or 240 volt AC power line and the DAS is electrically coupled via a data bus to a data processing system (typically a computer) for receiving data from the DAS and generating CT images. In addition, a control/status bus electrically couples the X-ray tube and the other support systems carried by the rotatable disk to control systems mounted on the support frame or peripheral to the support frame in order to permit control and status signals to be transferred. Typically, this can be accomplished either by using a power and data cable or through the use of electrically conductive slip rings in contact with electrically conductive brushes. In addition, data and control/status information can be transferred using wireless or radio frequency communications systems such as that disclosed in commonly owned U.S. Pat. No. 5,577,026, entitled APPARATUS FOR TRANSFERRING DATA TO AND FROM A MOVING DEVICE, which is hereby incorporated by reference. If a power cable is used, the disk cannot be rotated more than one revolution (360 degrees) and must be rotated back between scans. Slip rings permit the disk to rotate continuously in one direction and are therefore preferred. However, extensive wear of the slip rings and brushes results from their continuous sliding contact, thereby necessitating frequent replacement of the slip rings and/or the brushes and increasing the maintenance and operation costs of such systems. Furthermore, environmental factors, such as airborne dust and humidity, can limit the useful life of the slip rings and brushes as well as adversely affect quality of the electrical signals and power transferred.

In addition, environmental factors, such as temperature and humidity, affect the overall operation of the CT scanning system. The X-ray radiation detectors and the electronic circuits used to process the signals generated by the detectors are sensitive to changes in temperature and humidity and must either be continuously recalibrated or compensated for with additional circuitry. The recalibration process can be time consuming and limit the amount of time the CT scanner can perform its primary function of diagnosing patients. Compensation circuitry adds to the cost and complexity of the overall system.

Accordingly, it is an object of the present invention to provide an improved CT scanning system.

Another object of the present invention is to provide an improved CT scanning system that can be operated under a wider range of environmental conditions.

And another object of the present invention is to provide an improved CT scanning system that can operate reliably and accurately under a wide range of environmental conditions.

Still another object of the present invention is to provide an improved CT scanning system that is less susceptible to environmental effects such as temperature, humidity and dust.

SUMMARY OF THE INVENTION

In accordance with the present invention, the tomography apparatus includes a rotatable disk supported for rotation about an axis by a support frame. The support frame and the rotatable disk are enclosed by an enclosure which forms a substantially sealed chamber around the rotatable disk. The rotatable disk remains rotatable inside the chamber via a drive system having at least a portion thereof located inside the chamber. The tomography apparatus also includes an air conditioning system which processes the air inside the chamber to add or remove heat and/or moisture from air in the chamber. The air processed by the air conditioning system is recirculated into the chamber whereby substantially no air from outside the chamber is introduced into the chamber.

The tomography apparatus can include slip rings for electrically coupling signal processing components of the tomography apparatus mounted on the rotatable disk to signal processing components mounted on the support frame or located peripherally to the tomography apparatus. The slip rings can be located inside the chamber. The tomography apparatus can further include radiation detectors and signal processing systems which can be located inside the chamber, either fastened to the rotatable disk or fastened to the support frame.

In an alternative embodiment, the tomography apparatus includes a rotatable disk supported for rotation about an axis by a support frame. The support frame and the rotatable disk are enclosed by an enclosure which forms a substantially sealed chamber around the rotatable disk. The rotatable disk remains rotatable inside of said chamber via a drive system having at least a portion thereof located inside the chamber. The tomography apparatus also includes an air conditioning system which processes the air inside the chamber to add or remove heat and/or moisture from air in the chamber. The tomography apparatus further includes a system for maintaining the air pressure inside the chamber to be greater than the air pressure outside the chamber. The air processed by the air conditioning system is recirculated into the chamber whereby substantially no air from outside the chamber is introduced into the chamber. In order to replace any air that might leak out of the chamber, the system can further include an air input and filtering system whereby any additional air needed to maintain the air pressure inside the chamber to be greater than the pressure outside the chamber can be drawn from outside the chamber and passed through the filtering system.

The air conditioning system can include a first heat exchanger coupled to the chamber for adding or removing heat from the air inside to the chamber and a second heat exchanger coupled to the first heat exchanger to transfer the heat from the first heat exchanger to the outside air or transfer heat from the outside air to the first heat exchanger.

The air conditioning system can include a condenser for removing moisture from the air inside the chamber. The air conditioning system can further include a humidifier for adding moisture to the air inside the chamber.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE PREFERRED EMBODIMENTS

Figure 1:
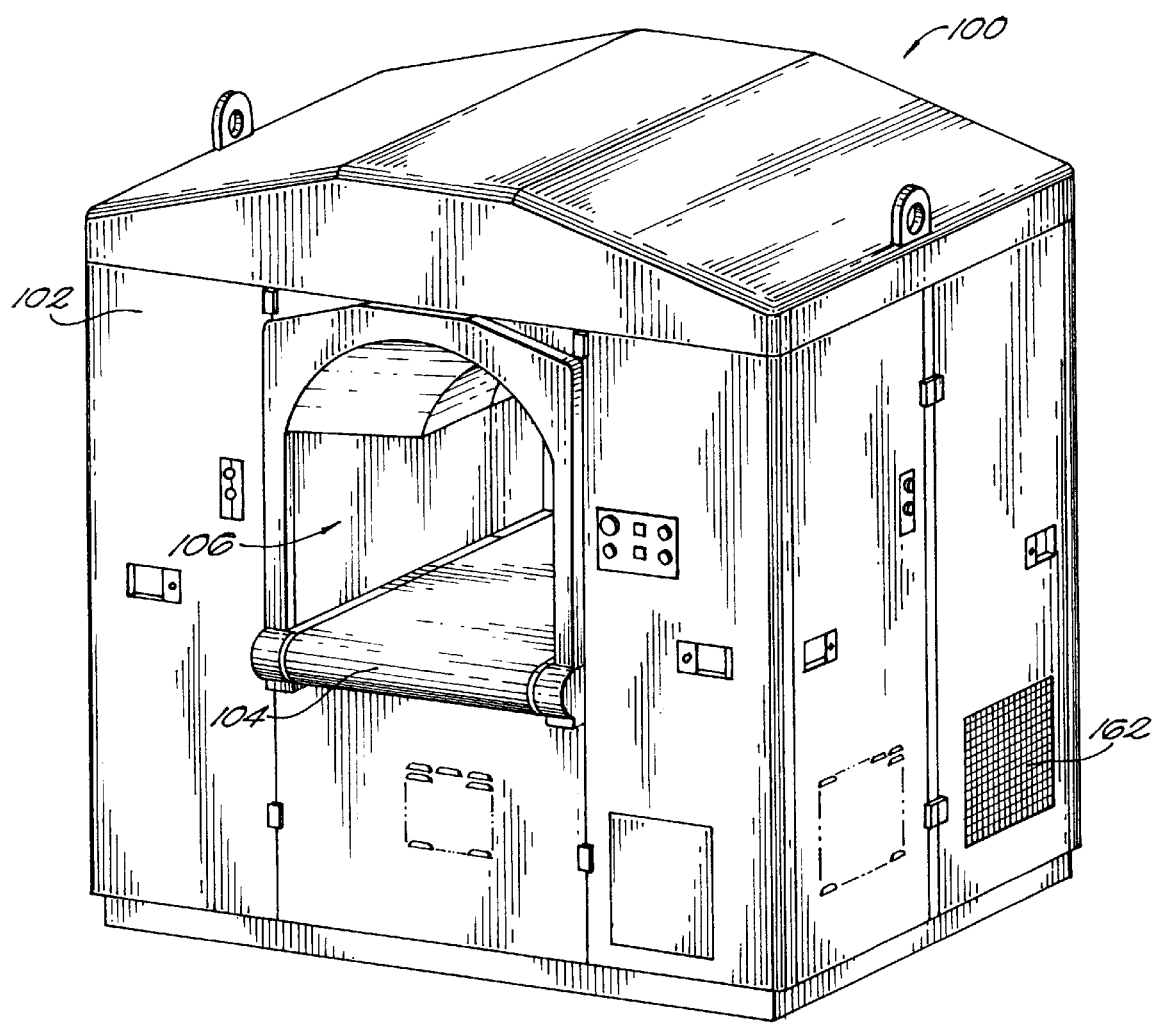
FIG. 1 is a perspective view showing the front of computed tomography scanner in accordance with the present invention.
Figure 2A:
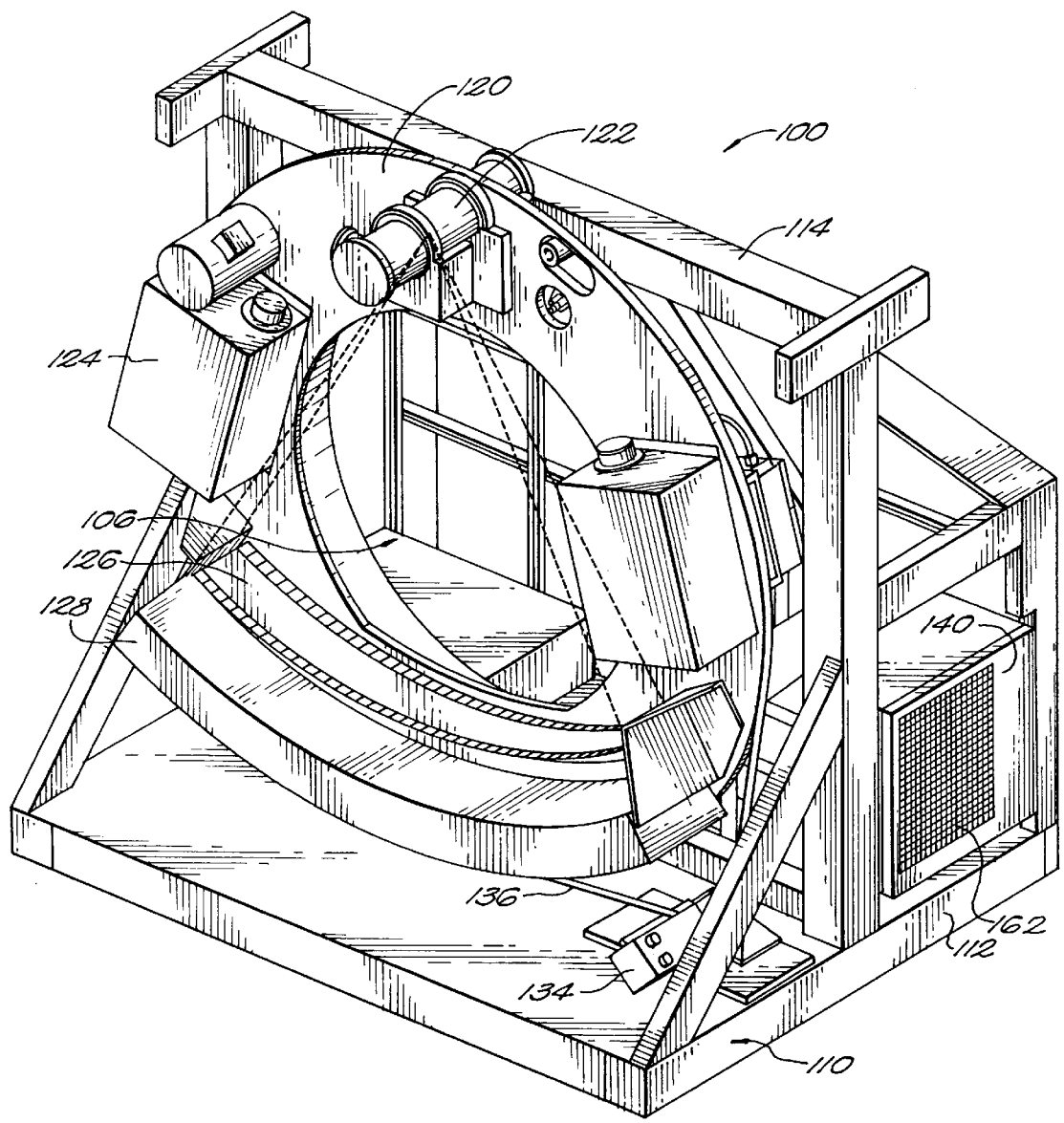
FIG. 2A is a perspective view showing the computed tomography scanner of FIG. 1 with the enclosure removed.
Figure 2B:
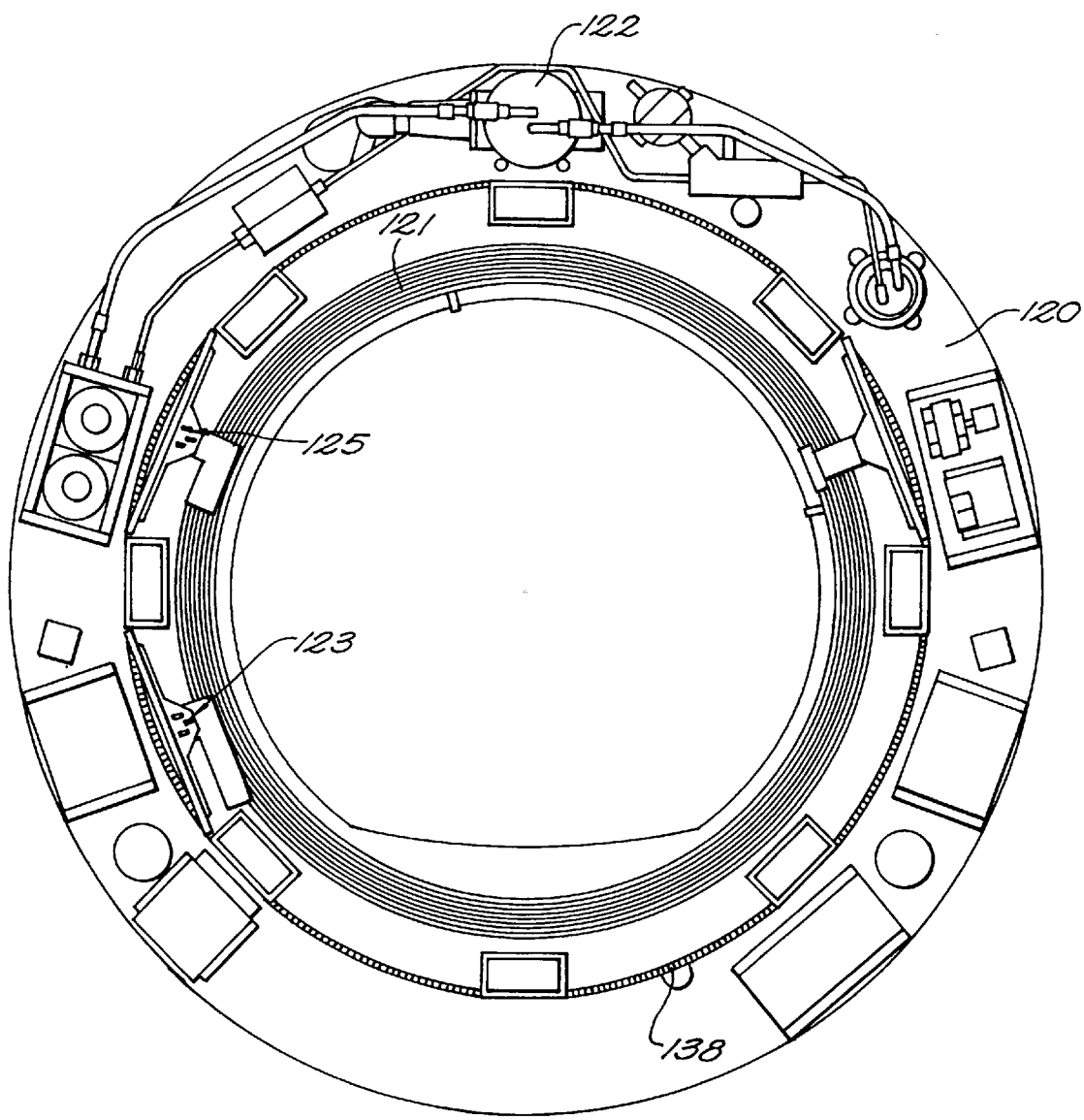
FIG. 2B is a rear view of the rotatable disk of the computed tomography scanner of FIG. 2A.

FIGS. 1, 2A and 2B show a CT scanning system 100 in accordance with the present invention. The CT scanning system 100 includes an enclosure 102 supported by support frame 110. The support frame 110 includes a base portion 112 and an upright portion 114. The upright portion 114 supports the rotatable disk 120 via bearings (shown at 115 in FIGS. 3 and 4) that permit the disk 120 to rotate freely about an axis (shown at 108 in FIGS. 3 and 4) relative to the support frame 110. The rotatable disk 120 includes an X-ray source 122, source support electronics 124 for controlling and powering the X-ray source, a detector array 126 and detector support electronics 128 secured to a peripheral portion thereof. A motor 134 and drive belt 136 provide controlled rotation of the rotatable disk 120 and position sensor 138 tracks the position of the rotatable disk 120. The rotatable disk 120 also includes a central opening 106 where objects to be scanned can be positioned. Electric power is transferred between the rotatable disk 120 and the support frame 110 via electrically conductive slip rings 121 coupled to the rotatable disk 120 in contact with electrically conductive brushes 123, 125 coupled to the support frame 110. An air conditioning system 140 is mounted to the support frame 110. The air conditioning system 140 includes a heat exhaust vent 162.

In the preferred embodiment, the CT scanning system 100 is intended to be used to scan luggage or baggage for the presence of explosives and/or other contraband, such as may be used at airports where the environments tend to be dusty. However, as one having ordinary skill in the art will appreciate, the present invention can be applied to other CT scanning systems such as medical CT scanners. In this embodiment, the CT scanning system 100 includes a conveyor 104 for transporting the baggage through the opening 106 in the rotatable disk 120. Sensors (not shown) can be provided adjacent to the opening 106 to detect the presence of baggage.

Figure 3:
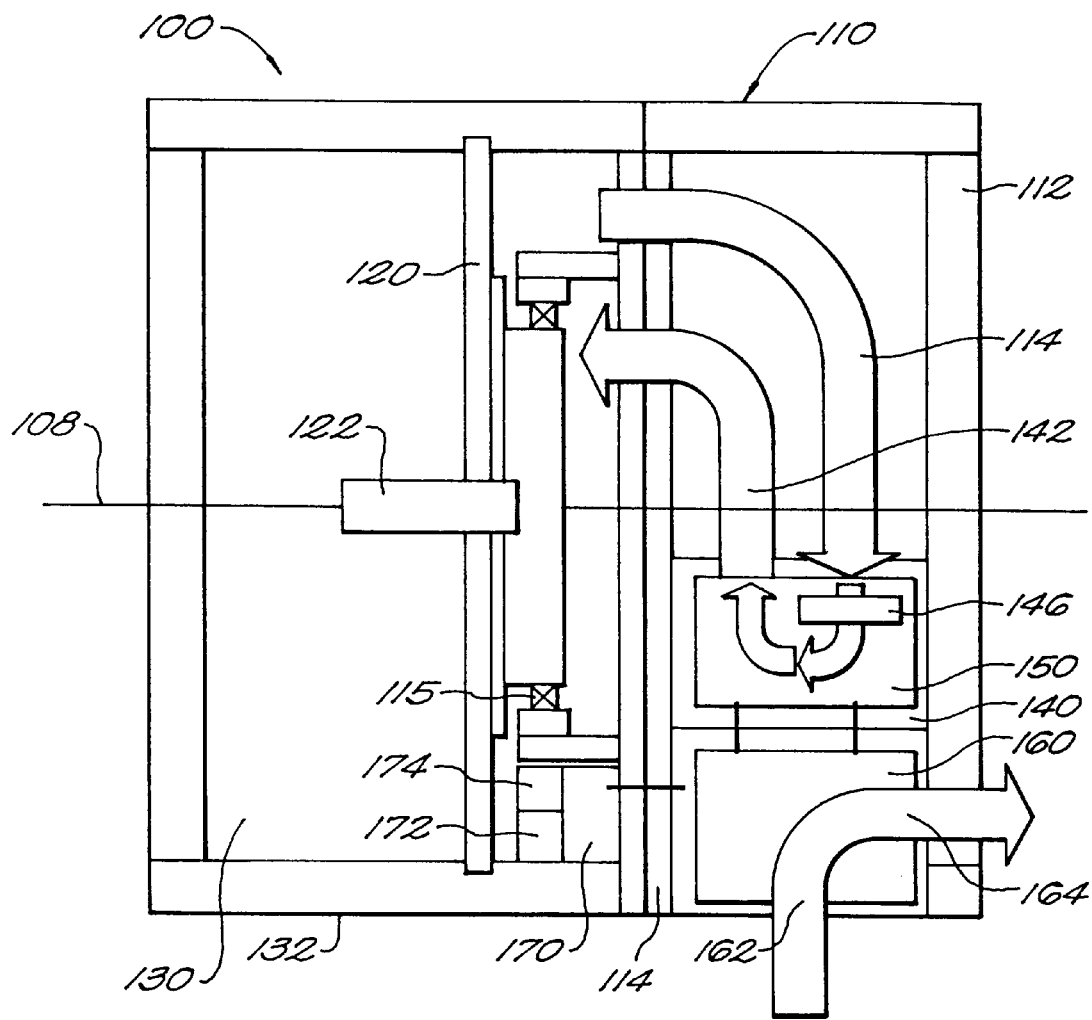
FIG. 3 is a diagrammatic top view of a computed tomography scanner in accordance with one embodiment of the present invention.

In accordance with one embodiment of the present invention, the enclosure 102 creates a substantially sealed chamber around the rotatable disk 120, while maintaining opening 106 to permit conveyor 104 to carry baggage through the central opening in the rotatable disk 120. With this arrangement dust and dirt in the environment is less likely to find its way into the moving parts of the machine. As shown in FIG. 3, the rotatable disk 120 is supported on bearings 115 for rotation about axis 108. The chamber 130, indicated by the bold line, is formed in part by the base portion 112 and the upright portion 114 of the support frame and by the enclosure (not shown). Air conditioning system 140 includes a cooling heat exchanger 150 and an exhaust heat exchanger 160. Cooling heat exchanger 150 is coupled to a cooling output duct 142 and a return duct 144. Cooling heat exchanger 150 receives air from the chamber 130 via return duct 144, removes heat from the air and supplies cool air into the chamber 130 via duct 142. Exhaust heat exchanger 160 includes an intake vent 162 and an exhaust vent 164 for exhausting heat received from the cooling heat exchanger. In addition, the air conditioning system 140 can include a condenser 146 which serves to remove moisture received from the chamber 130 before it is returned to the chamber 130.

Preferably, the tomography system includes an environmental control system 170 which is coupled to the air conditioning system 140 to control the operation of the air conditioning system 140 in order to maintain the temperature and humidity of the air in the chamber 130 at predefined levels. The environmental control system 170 can include a temperature sensor 172 and a humidity sensor 174 for monitoring the temperature and humidity of the air inside the chamber 130. The environmental control system 170 can include a computer system which receives signals from the sensors 172, 174 representative of the temperature and humidity of the air inside the chamber 130 and uses these signals to control the operation of the air conditioning system 140 to control the temperature and humidity of the air inside the chamber. Alternatively, environmental control system can include a thermostatic device and a humidistatic device for controlling the operation of the air conditioning system 140.

Figure 4:
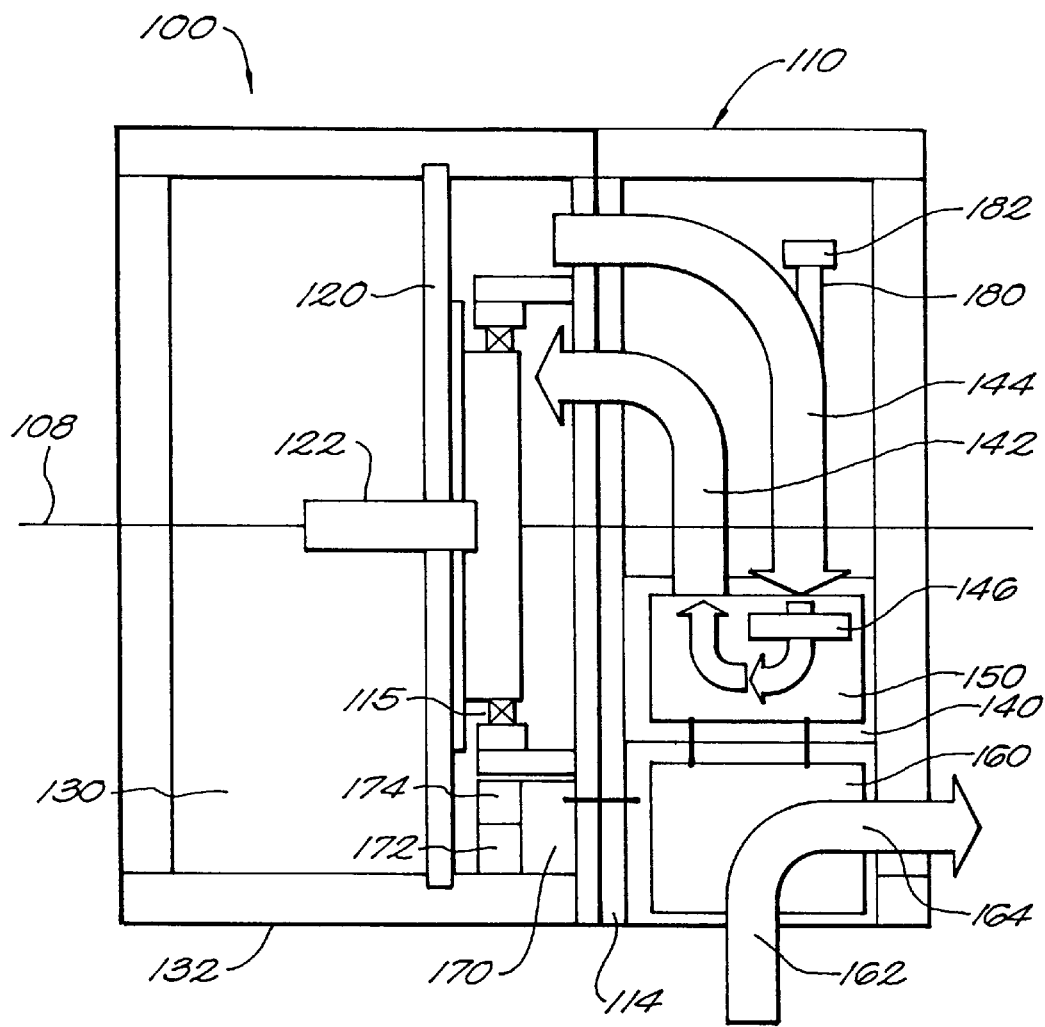
FIG. 4 is a diagrammatic top view of a computed tomography scanner in accordance with an alternate embodiment of the present invention.

FIG. 4 shows a CT scanning system 100 in accordance with an alternative embodiment of the present invention. In this embodiment, the air conditioning system 140 maintains the air pressure inside the chamber 130 to be slightly greater than the air pressure outside the chamber 130. This creates a positive pressure inside the chamber relative to the outside air and thus prevents dust and dirt from entering the chamber 130, a particularly helpful feature in such dusty environments as baggage areas in airports. The CT scanning system 100 shown in FIG. 4 is similar to that shown in FIG. 3, except that return duct 144 includes an input source 180 and a filter 182 to allow additional air to be introduced into the chamber. The additional air may be necessary to compensate for air that may leak through the enclosure 102.

Alternatively, the air conditioning system 130 can include a heating system for adding heat to the air in the chamber, such as where the operating environment of the system is extremely cold. The air conditioning system 130 can also include a humidifier to accommodate operation in dry environments. In another embodiment, the air conditioning system 130 can consist of a system that merely maintains the pressure inside the chamber 130 to be greater than the pressure outside the chamber 130.

In the preferred embodiment, the CT scanning system includes an air conditioning system 130 that operates continuously to cool the air in the chamber and no environmental control system is provided.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A tomography apparatus comprising:

a rotatable disk supported for rotation on a support frame;

an enclosure constructed and arranged so as to enclose at least a portion of the tomography apparatus including an array of detectors, and forming a substantially sealed chamber for the detectors; and an air conditioning system constructed and arranged so as recirculate and condition air circulated in said chamber so as to pressurized the air within the chamber without introducing harmful particulate matter into the chamber, control the humidity of the air within the chamber and remove heat from the detectors during the operation of the apparatus, said air conditioning system including a heat exchange subsystem coupled to said chamber and constructed and arranged so as to treat air in said chamber, and a humidifying subsystem for controlling the humidity of the air within the chamber.

2. An apparatus according to claim 1 further comprising slip rings for electrically coupling said rotatable disk to said support frame to permit power or data to be transferred between said rotatable disk and said support frame.

3. An apparatus according to claim 1 wherein said first heat exchange subsystem is constructed and arranged so as to receive air from said chamber, removing heat from said air and releasing said air to said chamber.

4. An apparatus according to claim 3 wherein said air conditioning system includes:

a second heat exchange subsystem coupled to said first heat exchange subsystem and constructed and arranged so as to transfer said heat to air outside of said chamber.

5. An apparatus according to claim 1 wherein said first heat exchange subsystem is coupled to said chamber and constructed and arranged so as to receive air from said chamber, adding heat to said air and releasing said air to said chamber.

6. An apparatus according to claim 1 wherein said subsystem includes:

a condensing subsystem coupled to said chamber and constructed and arranged so as to receive air from said chamber, removing moisture from said air and releasing said air to said chamber.

7. An apparatus according to claim 1 wherein said humidifying subsystem is coupled to said chamber and constructed and arranged so as to receive air from said chamber, adding moisture to said air and releasing said moister air to said chamber.

8. An apparatus according to claim 1 further comprising an environmental control constructed and arranged so as to control said air conditioning system.

9. An apparatus according to claim 1, further including a pump subsystem constructed and arranged so as to pump filtered air into the chamber so as to maintain the recirculating air within the chamber at a predetermined pressure.

10. An apparatus according to claim 1, further including a conveyor for conveying luggage through the tomography apparatus outside of the chamber.

* * * * *